United States Patent
Yamada

(10) Patent No.: US 12,100,138 B2
(45) Date of Patent: Sep. 24, 2024

(54) IMAGE PROCESSING APPARATUS, IMAGE PROCESSING METHOD, MEDICAL INFORMATION PROCESSING APPARATUS, MEDICAL INFORMATION PROCESSING METHOD, RADIATION IMAGING SYSTEM, AND COMPUTER-READABLE STORAGE MEDIUM

(71) Applicant: CANON KABUSHIKI KAISHA, Tokyo (JP)

(72) Inventor: Daisuke Yamada, Kanagawa (JP)

(73) Assignee: CANON KABUSHIKI KAISHA, Tokyo (JP)

( * ) Notice: Subject to any disclaimer, the term of this patent is extended or adjusted under 35 U.S.C. 154(b) by 609 days.

(21) Appl. No.: 17/342,615

(22) Filed: Jun. 9, 2021

(65) Prior Publication Data
US 2021/0295514 A1  Sep. 23, 2021

Related U.S. Application Data

(63) Continuation of application No. PCT/JP2019/043188, filed on Nov. 5, 2019.

(30) Foreign Application Priority Data

Dec. 14, 2018 (JP) .................. 2018-234710

(51) Int. Cl.
*G06T 7/12* (2017.01)
*A61B 6/00* (2006.01)
(Continued)

(52) U.S. Cl.
CPC .......... *G06T 7/0012* (2013.01); *A61B 6/5217* (2013.01); *A61B 6/54* (2013.01);
(Continued)

(58) Field of Classification Search
CPC ........ G06T 7/0012; G06T 2207/20081; G06N 20/00; G06N 3/08; A61B 6/5217; A61B 6/54
(Continued)

(56) References Cited

U.S. PATENT DOCUMENTS

2016/0350919 A1* 12/2016 Steigauf ................. G16H 40/20
2017/0213101 A1   7/2017 Rubens et al.
(Continued)

FOREIGN PATENT DOCUMENTS

| JP | H04-261649 A | 9/1992 |
| JP | H05-038334 A | 2/1993 |

(Continued)

OTHER PUBLICATIONS

Notice of Reasons for Refusal issued by the Japan Patent Office on Apr. 3, 2023 in corresponding JP Patent Application No. 2018-234710, with English translation.
(Continued)

*Primary Examiner* — Michael R Neff
(74) *Attorney, Agent, or Firm* — Carter, DeLuca & Farrell LLP

(57) ABSTRACT

An image processing apparatus comprises a first obtaining unit that obtains examination information, a readout unit that reads out learning result data selected based on the examination information from a storage unit storing at least one piece of learning result data that has been obtained by machine learning in advance, a second obtaining unit that obtains a medical image obtained based on the examination information obtained by the first obtaining unit, and a processing unit that processes the medical image obtained by the second obtaining unit using learning result data read out by the readout unit.

16 Claims, 6 Drawing Sheets

(51) Int. Cl.
*G06N 3/08* (2023.01)
*G06N 20/00* (2019.01)
*G06T 7/00* (2017.01)

(52) U.S. Cl.
CPC ............... *G06N 3/08* (2013.01); *G06N 20/00* (2019.01); *G06T 2207/20081* (2013.01)

(58) Field of Classification Search
USPC ........................................................ 382/128
See application file for complete search history.

(56) References Cited

U.S. PATENT DOCUMENTS

| | | | |
|---|---|---|---|
| 2020/0289215 A1* | 9/2020 | Maki | G16H 40/63 |
| 2021/0158105 A1 | 5/2021 | Machida et al. | |
| 2021/0158218 A1 | 5/2021 | Machida et al. | |

FOREIGN PATENT DOCUMENTS

| | | |
|---|---|---|
| JP | H09-179843 A | 7/1997 |
| JP | 2000-139889 A | 5/2000 |
| JP | 2004-73454 A | 3/2004 |
| JP | 2005-111249 A | 4/2005 |
| JP | 2005-118347 A | 5/2005 |
| JP | 2005-296065 A | 10/2005 |
| JP | 2008-167949 A | 7/2008 |
| JP | 2008-167950 A | 7/2008 |
| JP | 2011-50584 A | 3/2011 |
| JP | 2012-110693 A | 6/2012 |
| JP | 2013-102851 A | 5/2013 |
| JP | 2013-233420 A | 11/2013 |
| JP | 2014-474 A | 1/2014 |
| JP | 2017-185007 A | 10/2017 |
| WO | 2018015414 A1 | 1/2018 |
| WO | 2018/143180 A1 | 8/2018 |

OTHER PUBLICATIONS

International Search Report issued by the Japan Patent Office on Dec. 17, 2019 in corresponding International Application No. PCT/JP2019/043188, with English translation.

Extended European Search Report issued by the European Patent Office on Jun. 27, 2022 in corresponding EP Patent Application No. 19894761.6.

* cited by examiner

FIG. 4A

| | | LEARNING RESULT DATA | | | | | |
|---|---|---|---|---|---|---|---|
| | | A | B | C | D | E | ... |
| EXAMINATION INFORMATION | 1 | ○ | ○ | | | ○ | |
| | 2 | ○ | | ○ | ○ | ○ | |
| | 3 | ○ | | ○ | | | |
| | 4 | ○ | | ○ | ○ | | |
| | 5 | ○ | ○ | | | | |

○ : OBTAIN LEARNING RESULT DATA

FIG. 4B

| INFORMATION TYPE | CONTENT |
|---|---|
| ORDER INFORMATION | IMAGING PORTION AND IMAGING DIRECTION |
| OBJECT INFORMATION | BODY THICKNESS, HEIGHT, WEIGHT, GENDER, AND AGE |
| EXAMINATION TYPE | NORMAL EXAMINATION AND URGENT EXAMINATION (TRAUMA) |

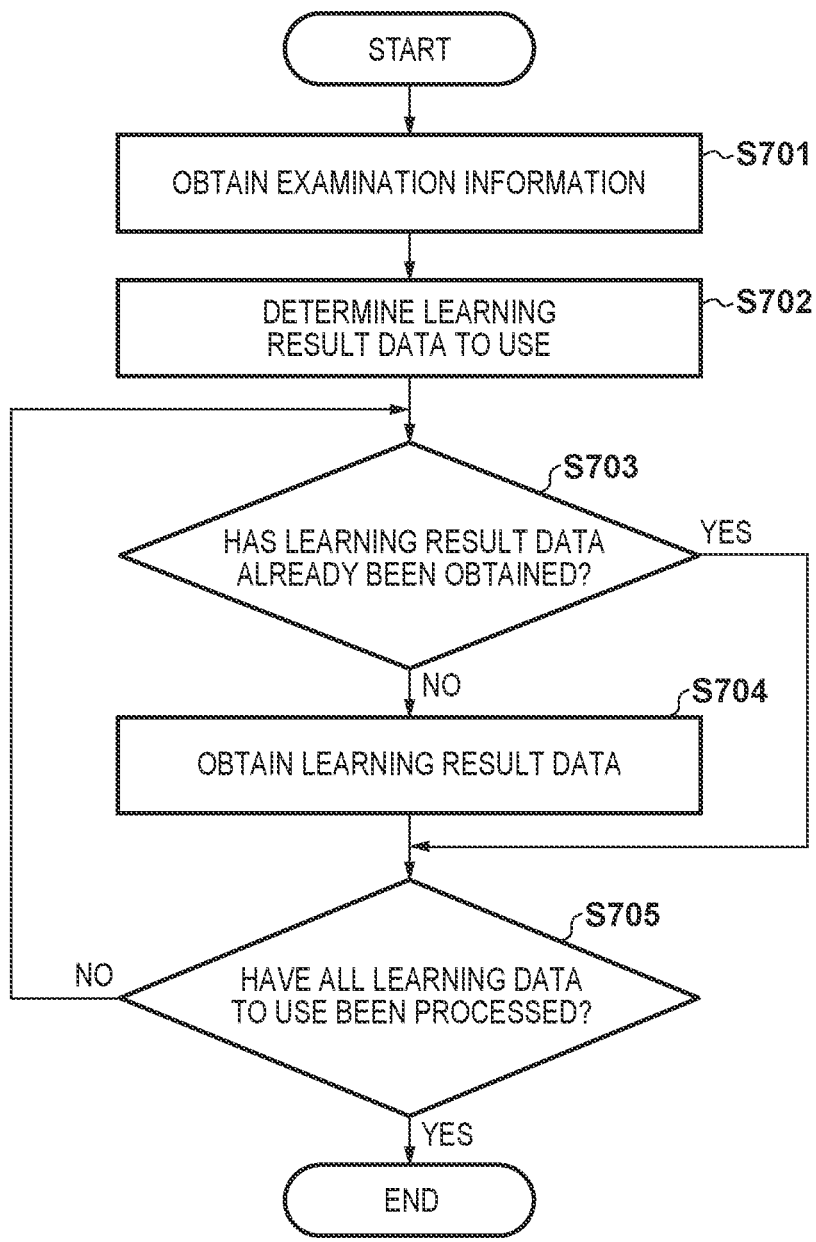

IMAGE PROCESSING APPARATUS, IMAGE PROCESSING METHOD, MEDICAL INFORMATION PROCESSING APPARATUS, MEDICAL INFORMATION PROCESSING METHOD, RADIATION IMAGING SYSTEM, AND COMPUTER-READABLE STORAGE MEDIUM

CROSS-REFERENCE TO RELATED APPLICATIONS

This application is a Continuation of International Patent Application No. PCT/JP2019/043188, filed Nov. 5, 2019, which claims the benefit of Japanese Patent Application No. 2018-234710, filed Dec. 14, 2018, both of which are hereby incorporated by reference herein in their entirety.

BACKGROUND OF THE INVENTION

Field of the Invention

The present invention relates to an image processing apparatus and an image processing method for processing medical images, a medical information processing apparatus that generates medical information, a radiation imaging system, and a computer-readable storage medium.

Background Art

Medical information processing apparatuses are known that have a function for providing information in accordance with user's tendency and preference using machine learning, a function for improving the image analysis accuracy, and the like. A method of detecting an object while improving the image recognition accuracy by machine learning is described in PTL 1. Also, a method of recognizing the dividing pattern, radiation field, imaging posture, and imaging portion of a radiation image, using a neural network, is described in PTL 2.

CITATION LIST

Patent Literature

PTL 1: Japanese Patent Laid-Open No. 2017-185007
PTL 2: Japanese Patent Laid-Open No. 4-261649

When a configuration is adopted in which inference processing by machine learning is to be performed in a medical information processing apparatus, learning result data that has been obtained by machine learning in advance needs to be input to an inference processing unit. When the amount of learning result data obtained by machine learning increases, it takes time for performing processing for reading learning result data from a storage medium such as a hard disk, and processing for extracting the read learning result data to a memory for making is possible to be used in the inference processing. Also, it is possible that many pieces of learning result data that are not needed in the inference processing are included, and processing quality deterioration is incurred. As a result, a suitable medical image cannot be quickly displayed, and the operability of the medical information processing apparatus degrades.

SUMMARY OF THE INVENTION

According to one aspect of the invention, a technique for realizing quick processing by selectively obtaining learning result data of machine learning according to examination information is provided.

According to one aspect of the present invention, there is provided an image processing apparatus comprising: a first obtaining unit configured to obtain examination information; a readout unit configured to read out learning result data selected based on the examination information from a storage unit that stores at least one piece of learning result data that has been obtained by machine learning in advance; a second obtaining unit configured to obtain a medical image obtained based on the examination information obtained by the first obtaining unit; and a processing unit configured to process the medical image obtained by the second obtaining unit using learning result data read out by the readout unit.

According to another aspect of the present invention, there is provided a medical information processing apparatus comprising: a first obtaining unit configured to obtain examination information; a readout unit configured to read out learning result data selected based on the examination information from a storage unit that stores at least one piece of learning result data that has been obtained by machine learning in advance; a second obtaining unit configured to obtain a medical image obtained based on the examination information obtained by the first obtaining unit; and a generating unit configured to generate medical information regarding the medical image obtained by the second obtaining unit using learning result data read out by the readout unit.

According to another aspect of the present invention, there is provided a radiation imaging system including a radiation detection apparatus and a control apparatus that controls the radiation detection apparatus, wherein the control apparatus includes: a first obtaining unit configured to obtain examination information; a readout unit configured to read out learning result data selected based on the examination information from a storage unit that stores at least one piece of learning result data that has been obtained by machine learning in advance; a second obtaining unit configured to obtain a radiation image obtained by imaging performed based on the examination information obtained by the first obtaining unit, from the radiation detection apparatus; and a processing unit configured to process the radiation image obtained by the second obtaining unit using learning result data read out by the readout unit.

According to another aspect of the present invention, there is provided an image processing method for a medical image comprising: obtaining examination information; reading out learning result data selected based on the obtained examination information from a storage unit that stores at least one piece of learning result data that has been obtained by machine learning in advance; obtaining a medical image obtained based on the obtained examination information; and processing the obtained medical image using learning result data read out in the reading.

According to another aspect of the present invention, there is provided a medical information processing method of processing medical information comprising: obtaining examination information; reading out learning result data selected based on the obtained examination information from a storage unit that stores at least one piece of learning result data that has been obtained by machine learning in advance; obtaining a medical image obtained based on the obtained examination information; and generating medical information regarding the obtained medical image using learning result data read out in the reading.

According to another aspect of the present invention, there is provided a non-transitory computer-readable storage medium storing a program for causing a computer to execute an image processing method for a medical image comprising: obtaining examination information; reading out learning result data selected based on the obtained examination information from a storage unit that stores at least one piece of learning result data that has been obtained by machine learning in advance; obtaining a medical image obtained based on the obtained examination information; and processing the obtained medical image using learning result data read out in the reading.

Further features of the present invention will become apparent from the following description of exemplary embodiments with reference to the attached drawings.

BRIEF DESCRIPTION OF THE DRAWINGS

The accompanying drawings, which are incorporated in and constitute a part of the specification, illustrate embodiments of the invention and, together with the description, serve to explain principles of the invention.

FIG. 4A is a diagram illustrating an example of learning result data obtaining information.

FIG. 4B is a diagram illustrating an example of examination information.

FIG. 6 is a flowchart illustrating processing for obtaining learning result data according to a third embodiment.

DESCRIPTION OF THE EMBODIMENTS

Hereinafter, suitable embodiments of the present invention will be described with reference to the accompanying drawings. Note that, in the following embodiments, the term "radiation" may include alpha rays, beta rays, gamma rays, particle rays, and cosmic rays, for example, in addition to X-rays. Also, the following embodiments can be combined as appropriate, and a configuration obtained by combining the embodiments as appropriate is included in the embodiments of the invention.

First Embodiment

Figure 1:
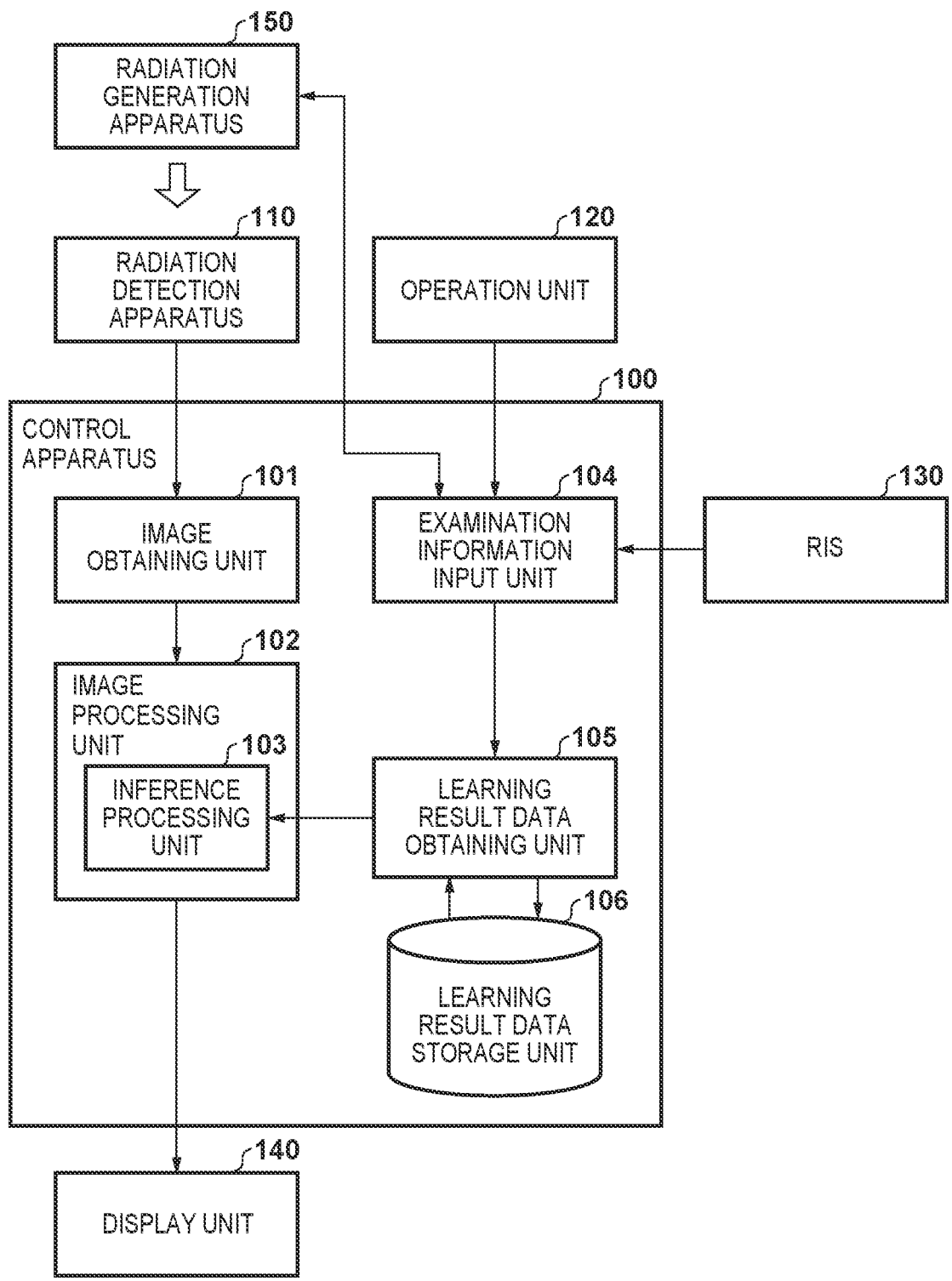
FIG. 1 is a diagram illustrating an exemplary configuration of a radiation imaging system according to a first embodiment.

FIG. 1 is a diagram illustrating an exemplary configuration of a radiation imaging system according to a first embodiment. The radiation imaging system includes a control apparatus 100, a radiation detection apparatus 110, an operation unit 120, an RIS (radiology information system) 130, a display unit 140, and a radiation generation apparatus 150. The control apparatus 100 is connected to the RIS 130, and controls radiation imaging using the radiation detection apparatus 110 and the radiation generation apparatus 150.

The radiation detection apparatus 110 detects radiation that has been emitted from the radiation generation apparatus 150 and transmitted through an examinee (not illustrated), and outputs image data according to the radiation. Note that this image data may also be rephrased as a medical image or a radiation image. Specifically, the radiation detection apparatus 110 detects the radiation transmitted through the examinee as charges corresponding to the transmitted radiation dose. For example, a direct conversion sensor such as a-Se that directly converts radiation into charges or an indirect sensor that uses a scintillator such as CsI that converts radiation into visible light and a photoelectric conversion element such as a-Si is used as the radiation detection apparatus 110. Moreover, the radiation detection apparatus 110 generates image data by performing A/D conversion on the detected charges, and outputs the image data to the control apparatus 100.

The control apparatus 100 is connected to the radiation detection apparatus 110 via a wired or wireless network or a dedicated line, for example. The radiation detection apparatus 110 performs imaging by capturing the radiation generated by the radiation generation apparatus 150, and output image data to the control apparatus 100. The control apparatus 100 has application functions that operate on a computer. That is, the control apparatus 100 includes at least one processor and a memory, and realizes later-described functional units by the processor executing a program stored in the memory. Note that some of or all of the functional units may be realized by dedicated hardware. The control apparatus 100 generates an image by performing image processing on the image data output from the radiation detection apparatus 110, and displays the image in the display unit 140. The operation unit 120 receives instructions from an operator. Also, the control apparatus 100 has a function of controlling the constituent elements. The control apparatus 100 outputs an image to the display unit 140 and provides a graphical user interface using the display unit 140 while controlling the operations of the radiation detection apparatus 110.

The control apparatus 100 controls the timing at which the radiation generation apparatus 150 generates radiation, and the imaging condition of radiation. In the control apparatus 100, an image obtaining unit 101 controls the timing at which the radiation detection apparatus 110 obtains image data by imaging and the timing at which the image data is output. An examination information input unit 104 is an example of a first obtaining unit that obtains examination information. The examination information input unit 104 of the present embodiment receives an input of examination information that an operator has manually input via the operation unit 120, or receives an input of examination information that has been selected by a user from a plurality of pieces of examination information obtained from the RIS 130 using the operation unit 120. Examination information input to the examination information input unit 104 is managed in association with image data obtained by imaging performed by the radiation detection apparatus 110 based on the examination information.

A learning result data obtaining unit 105 reads out learning result data from a learning result data storage unit 106. The learning result data storage unit 106 stores learning result data obtained by machine learning using training images. Also, the learning result data obtaining unit 105 includes information for associating various words included in examination information and combinations of the words with learning result data stored in the learning result data storage unit 106. Therefore, the learning result data obtaining unit 105 can obtain learning result data to be used in processing performed by an image processing unit 102 (inference processing unit 103) based on a word included in the examination information. The learning result data obtaining unit 105 is an example of a readout unit that reads out learning result data that is selected based on the examination information from a storage unit (learning result data storage unit 106) that stores learning result data obtained by machine learning in advance.

The image obtaining unit 101 is an example of a second obtaining unit that obtains a medical image based on examination information obtained by the first obtaining unit (examination information input unit 104). In the present embodiment, a radiation image obtained by imaging performed by the radiation detection apparatus 110 is obtained as the medical image. The image processing unit 102 performs image processing such as noise removal on the image data output from the radiation detection apparatus 110. Also, the image processing unit 102 can also perform image processing such as trimming and rotation on the image output from the radiation detection apparatus 110. The inference processing unit 103 performs inference processing such as radiation field recognition and gradation processing using learning result data obtained by machine learning. The image processing unit 102 may include a plurality of inference processing units according to objects such as radiation field recognition and gradation processing, as the inference processing unit 103. The image processing unit 102 displays the image subjected to image processing in the display unit 140. The image processing unit 102 and the inference processing unit 103 are an example of a processing unit that performs processing on an obtained medical image using learning result data read out by the readout unit (learning result data obtaining unit 105).

Figure 2:
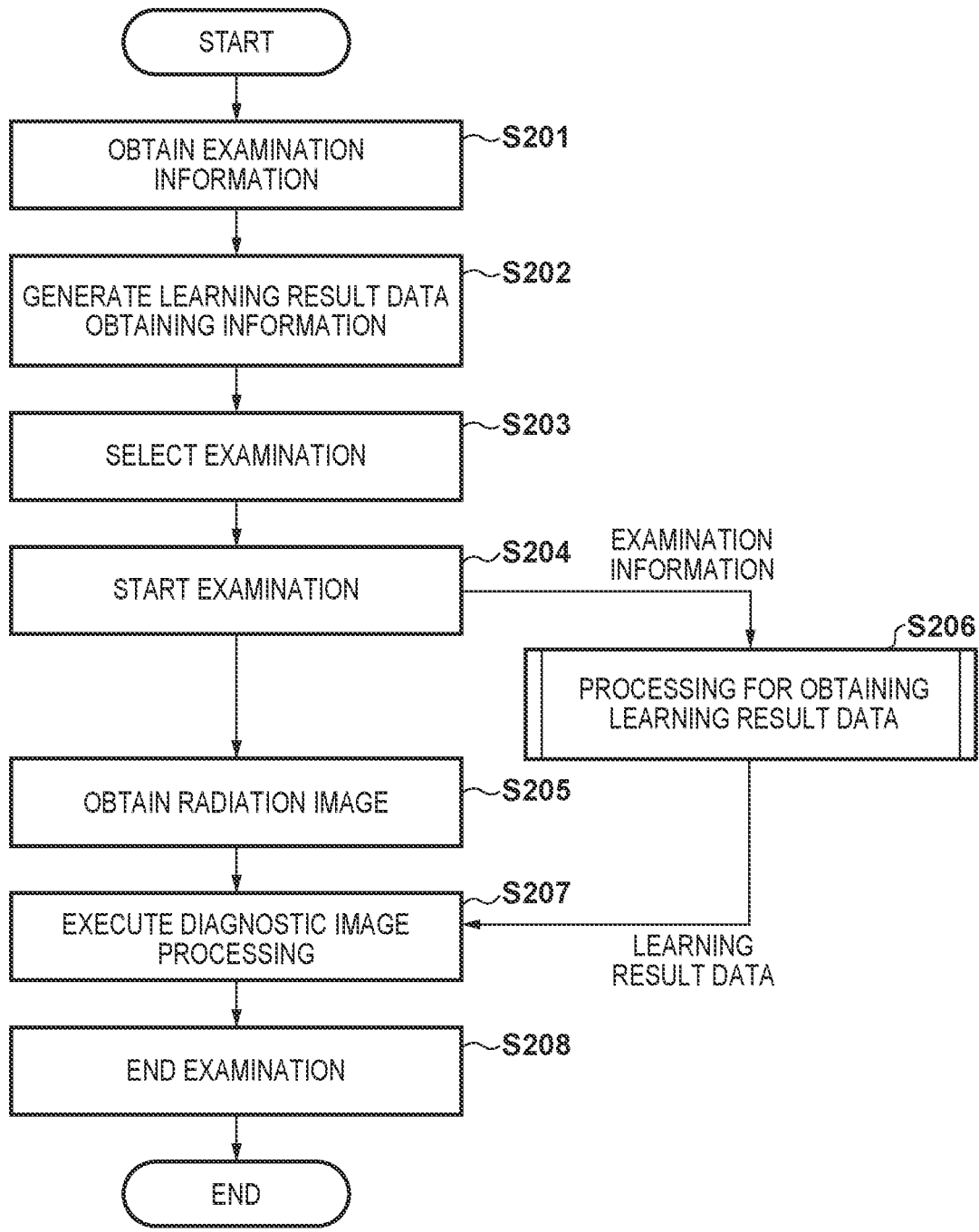
FIG. 2 is a flowchart illustrating imaging processing according to the first embodiment.

Next, the radiation image processing according to the first embodiment will be described following the flowchart in FIG. 2. In step S201, the examination information input unit 104 obtains a plurality of pieces of examination information from the RIS 130. In step S202, the learning result data obtaining unit 105 determines learning result data that should be read out with respect to each of the plurality of pieces of examination information obtained in step S201, and generates learning result data obtaining information indicating the correspondence between examination information and learning result data to be read out. The learning result data obtaining information will be described later with reference to FIG. 4A. In step S203, the examination information input unit 104 allows the user to select one of the plurality pieces of examination information obtained from the RIS 130, and sets the selected one as the examination target. Such processing can be realized by displaying the plurality pieces of acquired examination information in a list format, and by setting the selected examination information as the examination target in accordance with the operation input performed by the user for selecting one piece of examination information from the list, for example. Note that the configuration may be such that the user directly inputs the examination information from the operation unit 120. In this case, the selection operation in step S203 may not be needed.

In step S204, the control apparatus 100 starts examination by transmitting a signal for causing the radiation detection apparatus 110 to transition to a preparatory state in accordance with the set examination information. In response to this signal, the radiation detection apparatus 110 controls a bias power supply and applies a bias voltage to a two-dimensional image sensor using a main control circuit, for example. Thereafter, initialization in which an image signal is read out from the pixel array by a driving circuit is performed, in order to remove dark current accumulated in pixels. After the initialization is ended, the radiation detection apparatus 110 transmits state information indicating that a state in which preparation for obtaining a radiation image is finished is achieved to the control apparatus 100. Also, the control apparatus 100 (examination information input unit 104) sets operating parameters (such as tube voltage) of the radiation generation apparatus 150 based on the examination information selected in step S203. The control apparatus 100, upon receiving a notification that imaging preparation has been finished by the state information from the radiation detection apparatus 110, notifies the radiation generation apparatus 150 of exposure permission.

In step S205, the image obtaining unit 101 obtains a radiation image obtained by imaging performed by the radiation detection apparatus 110. Specifically, when the radiation generation apparatus 150 that has been notified of the exposure permission emits radiation in accordance with the operation of an exposure button, the driving circuit of the radiation detection apparatus 110 generates a radiation image by reading out an image signal obtained by detecting radiation that has been emitted, using the readout circuit, for example. The radiation detection apparatus 110 transmits the generated radiation image to the control apparatus 100. The image obtaining unit 101 of the control apparatus 100 receives the radiation image. In this way, the examination information input unit 104 and the image obtaining unit 101 of the control apparatus 100 function as a control unit that controls the operations of radiation imaging based on examination information, and obtains a radiation image obtained by the radiation imaging as the radiation image that is obtained by imaging based on the examination information.

On the other hand, in step S206, the learning result data obtaining unit 105 selectively obtains learning result data from the learning result data storage unit 106 based on the examination information selected in step S203 and the learning result data obtaining information generated in step S202. The details of the processing in step S206 will be described later with reference to the flowchart in FIG. 3. Here, the examination information includes at least one of order information, object information, and an examination type that are shown in FIG. 4B. For example, the order information includes an imaging portion and an imaging direction of the radiation imaging, the object information includes attributes of an object (e.g., body thickness, height, weight, gender, age), and the examination type includes a type indicating that the examination is which of a normal examination and an urgent examination. Note that the processing in step S205 may be executed in parallel to the processing (obtaining radiation image) in step S204.

In step S207, the image processing unit 102 executes diagnosis image processing on the radiation image obtained by the image obtaining unit 101. Here, the inference processing unit 103 executes inference processing by machine learning using the learning result data obtained in step S204. The inference processing unit 103 performs processing for determining a radiation field, processing for determining display contents such as an annotation to be superimposed on the image, and the like, by analyzing feature amounts of the image. Also, the configuration may be such that such processing results are displayed in the display unit 140, in the diagnosis image processing. In step S207, the control apparatus 100 ends the examination in response to an input operation made by the operator.

Figure 3:
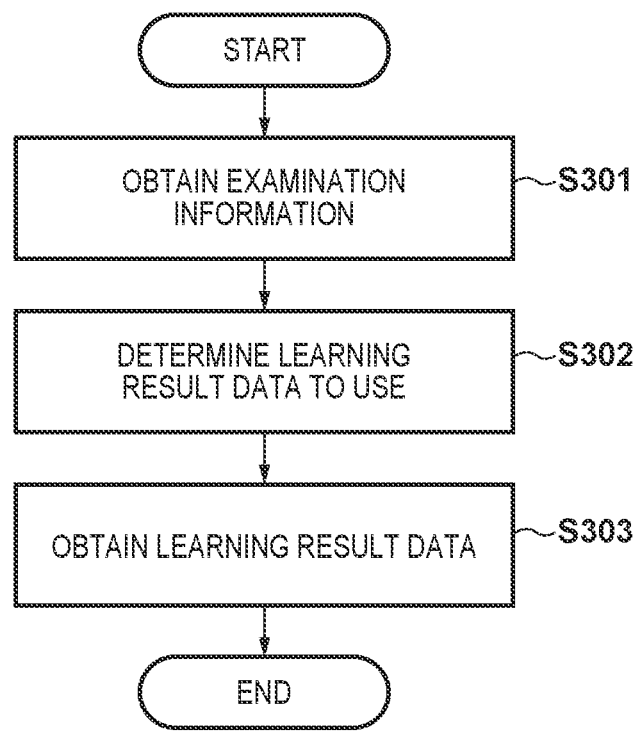
FIG. 3 is a flowchart illustrating processing for obtaining learning result data according to the first embodiment.

Next, the processing for obtaining learning result data performed by the learning result data obtaining unit 105 (processing in step S205) will be described with reference to the flowchart in FIG. 3. In step S301, the learning result data obtaining unit 105 obtains the examination information selected (determined) in step S203. In step S302, the learning result data obtaining unit 105 selects learning result data corresponding to the examination information obtained in step S301 by referring to the learning result data obtaining information that is generated and stored in step S202 in advance. Then, in step S303, the learning result data obtaining unit 105 reads out the learning result data selected in step S302 from the learning result data storage unit 106, performs extraction so as to be used in the inference processing unit 103, for example, and the extracted data is held by a holding unit, which is not illustrated.

The learning result data obtaining information includes contents shown in FIG. 4A, for example. According to the learning result data in FIG. 4A, the fact that, in the case of examination information [1], pieces of learning result data A, B, and E are to be obtained, and in the case of examination information [2], pieces of learning result data A, C, D, and E are to be obtained is shown. Moreover, the fact that, in the case of examination information [3], pieces of learning result data A and C are to be obtained is shown. The learning result data obtaining unit 105 selectively obtains needed learning result data in accordance with the examination information by referring to such learning result data obtaining information. For example, it is assumed that the learning result data A relates to the radiation field, the learning result data B relates to a chest anatomical feature, and the learning result data C relates to an abdomen anatomical feature, and the examination information [5] is an imaging order of chest frontal imaging. In this case, at least the learning result data C relating to the abdomen need not be obtained, and in the example in FIG. 4A, the learning result data obtaining information is configured such that the pieces of learning result data A and B are to be obtained. Therefore, if the examination information [5] is obtained in step S301, the learning result data obtaining unit 105 reads out the pieces of learning result data A and B from the learning result data storage unit 106 (steps S302 and S303).

As described above, according to the first embodiment, learning result data corresponding to examination information is selectively obtained from the learning result data storage unit 106, and therefore the time needed for obtaining needed learning result data can be reduced, and the processing of a radiation image by the image processing unit 102 can be quickly executed. Also, the image processing unit 102 can realize processing using suitable learning result data (e.g., inference processing). As a result, a desired medical image can be quickly obtained, and the operability of the medical image apparatus can be improved.

Second Embodiment

Figure 5:
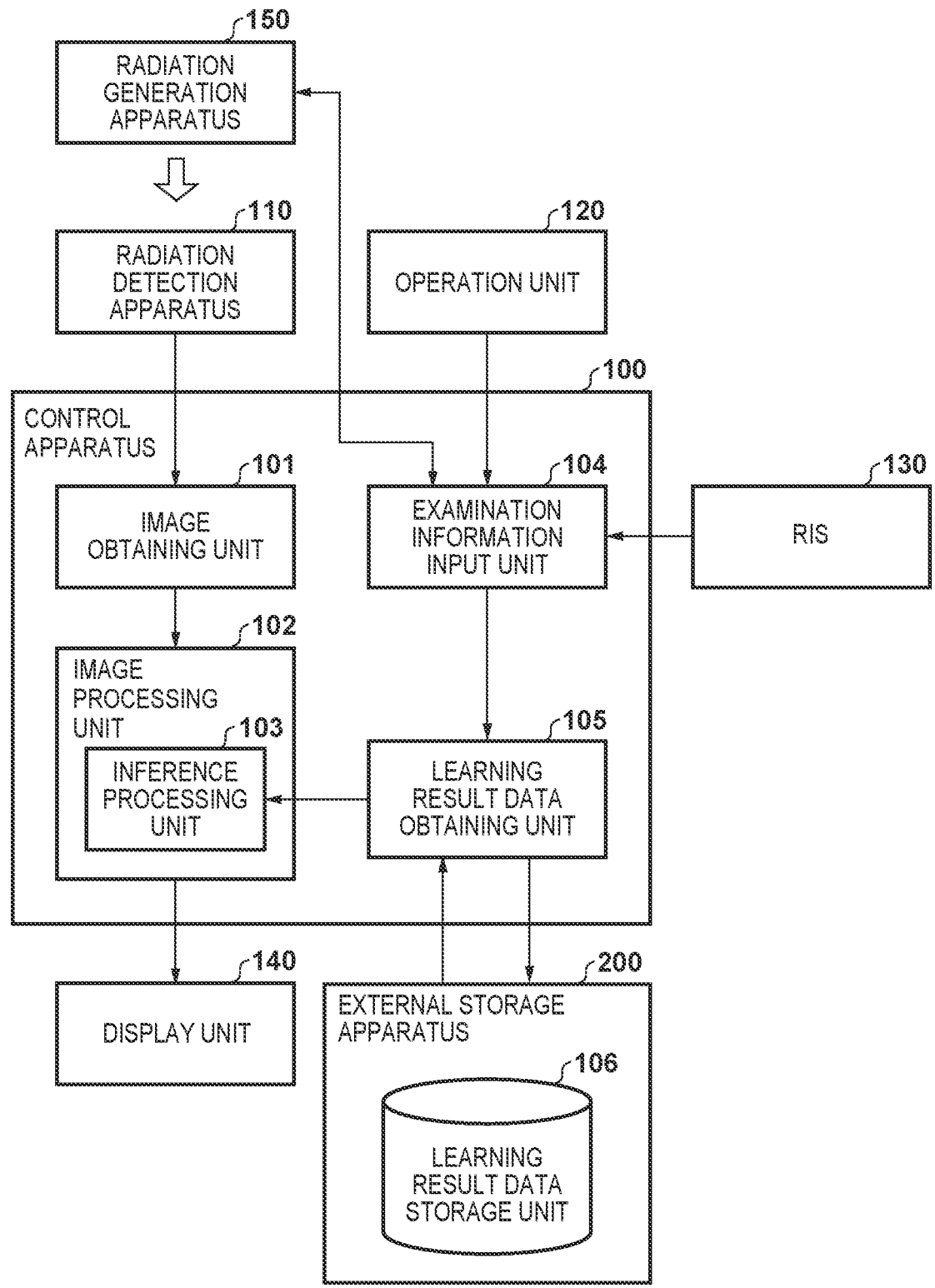
FIG. 5 is a diagram illustrating an exemplary configuration of a radiation imaging system according to a second embodiment.

In the first embodiment, a configuration in which the control apparatus 100 includes the learning result data storage unit 106 has been described (FIG. 1), but there is no limitation thereto. An external storage apparatus that can communicably connected to the control apparatus 100 may be provided with the learning result data storage unit 106. FIG. 5 is a block diagram illustrating an exemplary configuration of the radiation imaging system according to a second embodiment. In FIG. 5, the learning result data storage unit 106 is arranged in an external storage apparatus 200 that is provided outside the control apparatus 100. Note that, in FIG. 5, the constituent elements that are the same as those in the first embodiment are given the same reference numbers. The external storage apparatus 200 is a network storage, an external computer, or a cloud, for example.

In order for the control apparatus 100 to obtain learning result data, communication needs to be performed between the control apparatus 100 and the external storage apparatus 200, but the mode of this communication may be any mode such as wired or wireless communication.

According to the second embodiment as described above, similarly to the first embodiment, learning result data corresponding to examination information is selectively obtained, and therefore the operability of a medical image apparatus can be improved. Also, in the second embodiment, moreover, the learning result data can be shared with a control apparatus 100 in another facility, and therefore there is an advantage that the latest learning result data can be easily distributed and managed.

Third Embodiment

In the first embodiment, learning result data corresponding to the obtained examination information is selected by referring to learning result data obtaining information, and the selected learning result data is read out from the learning result data storage unit 106. In a third embodiment, control is performed such that, when the learning result data selected based on examination information has already been obtained, the selected learning result data will not be read out. As a result of avoiding duplicated readout of learning result data in this way, the processing load can be reduced. The configuration of the radiation imaging system according to the third embodiment is similar to that of the first embodiment (FIG. 1). In the following, the operations of a learning result data obtaining unit 105 according to the third embodiment will be described using the flowchart shown in FIG. 6. Note that the processing illustrated in FIG. 6 is to replace the processing described with reference to FIG. 3.

Similarly to the first embodiment, the learning result data obtaining unit 105 obtains the examination information selected in step S203 (step S701). Also, the learning result data obtaining unit 105 selects learning result data that should be obtained based on the obtained examination information and the learning result data obtaining information generated in step S202 (step S702).

The learning result data obtaining unit 105 includes a holding unit for holding the read-out learning result data. In steps S703 to S705, the learning result data obtaining unit 105 reads out learning result data that is not held by the holding unit, out of the pieces of learning result data selected based on the examination information in step S702, from the learning result data storage unit 106. First, in step S703, with respect to one of the pieces of learning result data that have been determined to be obtained in step S302, the learning result data obtaining unit 105 determines whether the one piece of learning result data has already been obtained. If it is determined that the one piece of learning result data has not been obtained in step S703, in step S704, the learning result data obtaining unit 105 reads out the one piece of learning result data from the learning result data storage unit 106. On the other hand, if it is determined that the one piece of learning result data has already been obtained in step S703, step S704 is skipped, and new readout of the one piece of learning result data is not performed. In step S705, the learning result data obtaining unit 105 determines whether or not the aforementioned processing has been performed with respect to all the pieces of learning result data selected in step S702, and if learning result data that has not been processed is present, returns the processing to step S703. If it is determined that all the pieces of selected learning result data have been processed in step S705, the processing shown in FIG. 6 is ended.

Note that, in the processing described above, whether or not learning result data is read out is determined according to whether or the learning result data that should be read out is held by the holding unit, but there is no limitation thereto.

For example, a configuration may be adopted in which pieces of learning result data other than the pieces of learning result data that are held by the holding unit are specified by referring to the learning result data obtaining information, and the specified pieces of learning result data are additionally read out and are held by the holding unit.

As described above, according to the third embodiment, not only learning result data corresponding to examination information is selectively obtained, but also only learning result data that has not been obtained, in examinations that are successively executed, is obtained, and as a result the learning result data can be obtained more quickly. Also, in a configuration in which the read-out learning result data is extracted to a form that can be used by the inference processing unit 103 and is held, it is also possible to avoid execution of duplicated extracting processing.

Fourth Embodiment

In the third embodiment, learning result data that has not been obtained is additionally obtained and held. Therefore, if a large amount of examination information is present, it is possible that the storage capacity of the holding unit of the learning result data obtaining unit 105 is in a tight situation. In a fourth embodiment, with respect to a group of pieces of learning result data that are in an exclusive relationship, only one of them is held, in any moment, and the occurrence of the storage capacity being in a tight situation in the holding unit is reduced. That is, the learning result data obtaining unit 105 operates such that, when learning result data selected based on examination information is read out, the learning result data that is in an exclusive relationship with the learning result data that is to be newly read out is discarded from the holding unit. In the following, the operations of a learning result data obtaining unit 105 according to the fourth embodiment will be described. Note that the configuration of the radiation imaging system is similar to that of the first embodiment (FIG. 1).

The operations of the learning result data obtaining unit 105 in the control apparatus 100 will be described using learning result data obtaining information shown in FIG. 4A and the flowchart shown in FIG. 6. In the example in FIG. 4A, the pieces of learning result data B and C are used for inference processing of the same object, and are used exclusively. Relation information indicating that the pieces of learning result data B and C are in an exclusive relationship is stored in the learning result data obtaining information. The learning result data obtaining unit 105 obtains and discards learning result data according to the examination information and this relation information. That is, the learning result data obtaining unit 105 obtains learning result data in step S704, and also if learning result data that is in an exclusive relationship with the obtained learning result data is held, discards the held learning result data.

For example, in FIG. 4A, when examinations are performed in the order of pieces of examination information [1], [2], and [3], in the examination information [1], pieces of learning result data A, B, and E are obtained and are input to the inference processing unit 103. In the next examination information [2], because the pieces of learning result data A and E have already been obtained, pieces of learning result data C and D are obtained and are input to the inference processing unit 103. Here, the held learning result data B is in an exclusive relationship with the obtained learning result data C, and therefore is discarded. In the next examination information [3], because the pieces of learning result data A and C have already been input to the inference processing unit 103, the learning result data obtaining processing can be omitted. Note that the combination of pieces of learning result data that are in an exclusive relationship may be determined from the learning result data obtaining information generated in step S202, or may be set in advance.

As described above, according to the fourth embodiment, regarding the processing for obtaining learning result data to be used for inference processing of the same object, discarding of learning result data is performed based on an exclusive relationship between pieces of learning result data. Therefore, the occurrence of the storage capacity being in a tight situation in the holding unit of the learning result data obtaining unit 105 can be reduced. Note that pieces of learning result data that are needed regardless of the examination information may be treated as essential, and the other pieces of learning result data may be treated as optional. In this case, with respect to optional pieces of learning result data, any of them may be selected according to the quality and accuracy of the radiation image that are requested by the user. Alternatively, with respect to the optional pieces of learning result data, the usage fee may be charged separately.

Fifth Embodiment

In the first embodiment, as a result of the processing in steps S301 to S303, learning result data corresponding to examination information is obtained and is used for inference processing. In a fifth embodiment, a learning result data obtaining unit 105 of a control apparatus 100 specifies pieces of learning result data (pieces of learning result data to be selected with respect to all the pieces of examination information) that are to be used independent of the examination information, and reads out and holds the specified pieces of learning result data regardless of the selection of the examination information. Specifically, the specified pieces of learning result data are obtained by reading out from the learning result data storage unit 106 in advance to the selection of the examination information.

For example, in the learning result data obtaining information in FIG. 4A, the learning result data A is selected with respect to all the pieces of examination information. For example, the learning result data A is a learning result regarding the radiation field, and is learning result data to be used in common in the inference processing for radiation field recognition to be performed in common with respect to the obtained radiation image in all the pieces of examination information. The learning result data obtaining unit 105 obtains such common learning result data in advance, for example, in advance to the selection of examination information in step S203. Also, in steps S301 to S303 in FIG. 3, the learning result data obtaining unit 105 obtains learning result data other than the pieces of learning result data obtained in advance according to the selected examination information.

As described above, according to the fifth embodiment, pieces of learning result data that are independent of the examination information can be obtained in advance to the start of examination, and therefore, the learning result data to be obtained at the time of performing imaging can be reduced, and the needed learning result data can be obtained more quickly.

According to the embodiments described above, the learning result data of machine learning to be used in inference processing is selectively obtained according to examination information, and a suitable medical image can be quickly displayed. As a result, the operability of the medical image apparatus can be improved. Also, even when the amount of learning result data to be used by the inference processing unit of machine learning increases, as a result of selectively obtaining learning result data corresponding to examination information from a storage apparatus such as a hard disk, the reading processing of learning result data and the extracting processing to a memory can be streamlined.

Note that, in the embodiments described above, an example has been described in which image processing such as radiation field recognition or gradation processing is performed on a medical image using learning result data, but there is no limitation thereto. For example, a medical information processing apparatus that generates medical information regarding a medical image using the obtained learning result data may be provided. Here, the medical information is diagnosis support information such as segmentation in a medical image or a lesioned part detected in a medical image, for example. In this case, the medical information processing apparatus obtains examination information, and reads out learning result data selected based on the examination information from a storage unit that stores at least one piece of learning result data obtained by machine learning in advance. Also, the medical information processing apparatus obtains a medical image that has been obtained based on the obtained examination information, and generates medical information using the learning result data read out from the storage unit, with respect to the obtained medical image. According to such a configuration, as a result of selectively obtaining and using learning result data of machine learning according to examination information, medical information regarding a medical image can be quickly displayed.

According to the present invention, quick processing can be realized by selectively obtaining learning result data of machine learning according to examination information.

OTHER EMBODIMENTS

Other Embodiments

Embodiment(s) of the present invention can also be realized by a computer of a system or apparatus that reads out and executes computer executable instructions (e.g., one or more programs) recorded on a storage medium (which may also be referred to more fully as a 'non-transitory computer-readable storage medium') to perform the functions of one or more of the above-described embodiment(s) and/or that includes one or more circuits (e.g., application specific integrated circuit (ASIC)) for performing the functions of one or more of the above-described embodiment(s), and by a method performed by the computer of the system or apparatus by, for example, reading out and executing the computer executable instructions from the storage medium to perform the functions of one or more of the above-described embodiment(s) and/or controlling the one or more circuits to perform the functions of one or more of the above-described embodiment(s). The computer may comprise one or more processors (e.g., central processing unit (CPU), micro processing unit (MPU)) and may include a network of separate computers or separate processors to read out and execute the computer executable instructions. The computer executable instructions may be provided to the computer, for example, from a network or the storage medium. The storage medium may include, for example, one or more of a hard disk, a random-access memory (RAM), a read only memory (ROM), a storage of distributed computing systems, an optical disk (such as a compact disc (CD), digital versatile disc (DVD), or Blu-ray Disc (BD)™), a flash memory device, a memory card, and the like.

While the present invention has been described with reference to exemplary embodiments, it is to be understood that the invention is not limited to the disclosed exemplary embodiments. The scope of the following claims is to be accorded the broadest interpretation so as to encompass all such modifications and equivalent structures and functions.

The invention claimed is:

1. An image processing apparatus comprising:
at least one of (a) one or more processors connected to one or more memories storing a program including instructions executed by the one or more processors and (b) circuitry configured to function as:
reading out a plurality pieces of learning result data selected based on examination information, the plurality pieces of learning result data having been obtained by machine learning and including learning result data regarding radiation field recognition and learning result data regarding detection of an object part or a lesioned part; and
processing a medical image using the read out plurality pieces of learning result data, the medical image being obtained based on the examination information.

2. The image processing apparatus according to claim 1, wherein the at least one of (a) one or more processors and (b) circuitry is configured to function as: controlling operations of radiation imaging based on the examination information; and
obtaining a radiation image obtained by the radiation imaging as a medical image obtained by imaging based on the examination information.

3. The image processing apparatus according to claim 1, wherein the examination information includes at least one of order information including an imaging portion and an imaging direction of radiation imaging, object information regarding an attribute of an object, and information indicating an examination type including classification between a normal examination and an urgent examination.

4. The image processing apparatus according claim 1, further comprising the storage unit.

5. The image processing apparatus according to claim 1, wherein the at least one of (a) one or more processors and (b) circuitry is configured to function as reading out learning result data from the storage unit that is externally provided.

6. The image processing apparatus according to claim 1, wherein the plurality pieces of learning result data includes, as one set, (i) learning result data regarding the radiation field recognition and (ii) at least one piece of learning result data selected among learning result data regarding detection of a plurality of types of object parts or lesioned parts that differs based on the examination information.

7. An image processing apparatus comprising:
at least one of (a) one or more processors connected to one or more memories storing a program including instructions executed by the one or more processors and (b) circuitry configured to function as:
reading out learning result data selected based on examination information from a storage unit that stores at least one piece of learning result data that has been obtained by machine learning, the examination information being selected one of a plurality pieces of examination information according to an instruction from a user;
obtaining a medical image obtained based on the selected examination information; and processing the obtained medical image using the read out learning result data.

8. The image processing apparatus according to claim 7, wherein the at least one of (a) one or more processors and (b) circuitry is further configured to function as:
reading out learning result data corresponding to the selected examination information by referring to learning result data obtaining information, from the storage unit, the learning result data obtaining information indicating correspondence between examination information and learning result data to be read out.

9. The image processing apparatus according to claim 8, wherein the at least one of (a) one or more processors and (b) circuitry is further configured to function as:
holding the read out learning result data;
specifying learning result data that is not the held learning result data by referring to the learning result data obtaining information; and
additionally reading out the specified learning result data.

10. The image processing apparatus according to claim 8, wherein the at least one of (a) one or more processors and (b) circuitry is configured to function as: specifying learning result data to be used independent of examination information from the learning result data obtaining information; and
reading out the specified learning result data regardless of the selection of examination information.

11. The image processing apparatus according to claim 10, wherein the at least one of (a) one or more processors and (b) circuitry is configured to function as reading out the specified learning result data, in advance, from the storage unit in advance to the selection of examination information.

12. An image processing apparatus comprising:
at least one of (a) one or more processors connected to one or more memories storing a program including instructions executed by the one or more processors and (b) circuitry configured to function as:
reading out learning result data selected based on examination information from a storage unit that stores at least one piece of learning result data that has been obtained by machine learning;
holding the read out learning result data;
obtaining a medical image obtained based on the examination information;
processing the obtained medical image using the read out learning result data; and
reading out, out of pieces of learning result data selected based on the examination information, learning result data that is not held, from the storage unit.

13. The image processing apparatus according to claim 12, wherein the at least one of (a) one or more processors and (b) circuitry is further configured to function as, when reading out learning result data selected based on examination information, discarding learning result data that is in an exclusive relationship with learning result data that is newly read out.

14. A radiation imaging system including a radiation detection apparatus and a control apparatus that controls the radiation detection apparatus, wherein the control apparatus includes:
at least one of (a) one or more processors connected to one or more memories storing a program including instructions executed by the one or more processors and (b) circuitry configured to function as:
reading out a plurality pieces of learning result data selected based on examination information, the plurality pieces of learning result data having been obtained by machine learning and including learning result data regarding radiation field recognition and learning result data regarding detection of an object part or a lesioned part; and
processing a radiation image using the read out plurality pieces of learning result data, the medical image being obtained based on the examination information.

15. An image processing method for a medical image comprising:
reading out a plurality pieces of learning result data selected based on examination information, the plurality pieces of learning result data having been obtained by machine learning and including learning result data regarding radiation field recognition and learning result data regarding detection of an object part or a lesioned part; and
processing a medical image using the read out plurality pieces of learning result data, the medical image being obtained based on the examination information.

16. A non-transitory computer-readable storage medium storing a program for causing a computer to execute an image processing method for a medical image comprising:
reading out a plurality pieces of learning result data selected based on examination information, the plurality pieces of learning result data having been obtained by machine learning and including learning result data regarding radiation field recognition and learning result data regarding detection of an object part or a lesioned part; and
processing a medical image using the read out plurality pieces of learning result data, the medical image being obtained based on the examination information.

* * * * *